(12) United States Patent
Harris et al.

(10) Patent No.: US 10,806,881 B2
(45) Date of Patent: Oct. 20, 2020

(54) CRICOTHEROTOMY APPARATUS AND METHOD

(71) Applicant: Wolf Technical Services, Inc., Indianapolis, IN (US)

(72) Inventors: Amy Harris, McCordsville, IN (US); Zach Wagner, Noblesville, IN (US); Melissa Montgomery, Alexandria, IN (US); Adam Furore, Warsaw, IN (US)

(73) Assignee: Wolf Technical Services, Inc., Indianapolis, IN (US)

(*) Notice: Subject to any disclaimer, the term of this patent is extended or adjusted under 35 U.S.C. 154(b) by 420 days.

(21) Appl. No.: 15/643,970

(22) Filed: Jul. 7, 2017

(65) Prior Publication Data
US 2018/0008792 A1    Jan. 11, 2018

Related U.S. Application Data

(60) Provisional application No. 62/360,126, filed on Jul. 8, 2016.

(51) Int. Cl.
*A61M 16/04* (2006.01)
*A61B 17/3209* (2006.01)
*A61B 17/34* (2006.01)
*A61M 16/06* (2006.01)

(52) U.S. Cl.
CPC ... *A61M 16/0402* (2014.02); *A61B 17/32093* (2013.01); *A61B 17/3417* (2013.01); *A61M 16/0497* (2013.01); *A61M 16/0683* (2013.01)

(58) Field of Classification Search
CPC .......... A61B 17/3209; A61B 17/32093; A61B 2017/320052; A61B 2017/320056; A61M 16/0465; A61M 16/0472; A61M 16/0497
See application file for complete search history.

(56) References Cited

U.S. PATENT DOCUMENTS

| | | | | |
|---|---|---|---|---|
| 3,791,386 A * | 2/1974 | McDonald | ........ | A61M 16/0472 128/207.29 |
| 3,991,765 A * | 11/1976 | Cohen | ................ | A61M 16/0472 128/207.29 |
| 4,624,252 A * | 11/1986 | Weiss | ................ | A61M 16/0472 606/185 |
| 7,267,124 B1 * | 9/2007 | Roberson, Jr. | ..... | A61M 16/0472 128/207.29 |
| 7,347,840 B2 * | 3/2008 | Findlay | ................ | A61B 10/025 604/180 |
| 10,293,128 B2 * | 5/2019 | Wolf | .................. | A61B 17/3415 |
| 2008/0251083 A1 * | 10/2008 | Fetcenko | .......... | A61M 16/0472 128/207.29 |

(Continued)

*Primary Examiner* — Ryan J. Severson
(74) *Attorney, Agent, or Firm* — Maginot, Moore & Beck LLP

(57) ABSTRACT

A cricothyrotomy apparatus includes a frame, a protuberance, and a blade member. The frame includes a blade guide. The protuberance extends in a first direction from the frame, and is located at a distance from the blade guide that corresponds to the distance between a sternal notch of an adult human and an anterior cricothyroid membrane of the adult human. The protuberance is sized and configured to be at least partly received by a sternal notch of an adult human. The blade member is slideably disposed in the blade guide.

20 Claims, 6 Drawing Sheets

(56) References Cited

U.S. PATENT DOCUMENTS

| | | | |
|---|---|---|---|
| 2015/0182716 A1* | 7/2015 | Wolf | A61B 17/3415 |
| | | | 600/245 |
| 2016/0220772 A1* | 8/2016 | Krimsky | A61M 16/0472 |
| 2018/0008305 A1* | 1/2018 | Krimsky | A61M 16/0488 |
| 2018/0008792 A1* | 1/2018 | Harris | A61M 16/0402 |

* cited by examiner

CRICOTHEROTOMY APPARATUS AND METHOD

CROSS-REFERENCE TO RELATED APPLICATIONS

This application claims the benefit U.S. Provisional Application Ser. No. 62/360,126, filed Jul. 8, 2016.

STATEMENT REGARDING FEDERALLY SPONSORED RESEARCH OR DEVELOPMENT

This invention was made under a contract with the United States government Department of Defense under DOD Contract No. W81XWH-14-C-0012. The government has certain rights in the invention.

FIELD OF THE INVENTION

The present invention relates generally to cricothyrotomies and managing airway trauma.

DESCRIPTION OF THE RELATED ART

A cricothyrotomy is a medical procedure that involves creating an incision in the cricothyroid membrane. The cricothyroid membrane is a membrane in the neck proximate to what is commonly referred to as the Adam's Apple. One purpose of a cricothyrotomy is to create an emergency pathway to the lungs of a patient for respiration, when the normal pathway through the nose and/or mouth is compromised. After the incision in the cricothyroid membrane is completed, a tube is place through the incision site and into the patient's airway. The lungs of the patient may then exchange gas (inhale and exhale) through the tube.

Cricothyrotomies are of particular use when time is critical and access to immediate hospital care is not available. Such situations can include, but are not limited to, combat and disaster site situations. Cricothyrotomy kits contain devices that assist in the cricothyrotomy procedure, and are often provided to first responders and field medical personnel.

One popular prior art cricothyrotomy kit contains only the basic tools needed to perform an emergency cricothyrotomy. Such kits contain a scalpel, a hook device, and a tube. The scalpel is used to cut the cricothyroid membrane, and the hook device is used to spread the spread the incision site to allow insertion of the tube. While this is technically sufficient, the included tools provide scant protection against many of the common errors that are encountered while performing this procedure on the battlefield, such as misidentification of anatomical landmarks, posterior tracheal perforation, and mediolateral misalignment. In addition, the components are loosely packaged in the kit, relying on the user to recall proper procedural order and equipment usage. This can easily become confusing for the user during a high-stress scenario.

Another kit, called the NuTrake is a kit that uses a split-needle design that expands the opening after puncture. This allows for one of three tracheal tubes to be inserted into the surgical airway. While the split needle design eliminates some of the confusion and stress associated with use of the hook device for spreading the opening, it still shares several shortcomings of the basic kit. For example, this device also relies on the manual location of the cricothyroid membrane by the medic or physician.

Other devices have attempted to address some of the issues of the basic cricothyrotomy kits, but have their own shortcomings. For example, one device punctures both the skin and the membrane using a sharp metal trocar/obturator that is nested in a plastic cannula. Upon successful puncture, a safety stopper is removed, and the trocar/obturator is removed, leaving behind the plastic cannula. In theory this approach seems to be very beneficial, as it can reduce procedure time compared to traditional approaches. However, in mid-procedure, the only safety stop (which limits the possibility of posterior tracheal perforation), is removed. At this time, the device is not yet fully inserted. The next step requires that the user carefully advance the plastic cannula forward while simultaneously retracting the sharp metal trocar/obturator. This technique may be sufficient for an emergency room or other hospital situation where the patient is secured. However, this method is risky in a battlefield scenario when the possibility of patient movement relative to the device during insertion is highly probable. In addition to this flaw in the device safety, the device also requires that the user angle the device during insertion to help prevent posterior tracheal wall perforation. Should the user omit this step or perform it incorrectly, the patient is at risk for additional injury.

Yet another device is an all-in-one device that incorporates several components of common cricothyrotomy kits into a single device, similar to a Swiss-Army® knife. Due to the amount of integrated functions, it is overly complicated and may increase procedure time if the user is not extensively trained. This design addresses some issues associated with having a loose collection of components. The device also partially automates the procedure by combining the scalpel and retractor device into essentially the same device. However, there are still several drawbacks with this tool. Most notably is the lack of an alignment mechanism for ensuring proper and consistent placement of the device in an anatomical frame of reference. The device, like all others investigated, still relies on the user to properly identify the underlying landmarks and choose the correct location to perform the incision and subsequent retraction. Additionally, in a study performed to evaluate the effectiveness of the tool, several users reported that the provided scalpel was of insufficient length to perform the procedure properly.

SUMMARY OF THE INVENTION

At least some embodiments address one or more drawbacks of the prior art by providing a cricothyrotomy kit that includes an anchored guide member configured to align a blade guide over the cricothyroid membrane. The aligned blade guide is configured to guide a blade of a blade member into the cricothyroid membrane, and limits the depth of travel of the blade member to a desired depth. The device greatly reduces the error in location of the incision, and the risks associated with an incision that is too shallow or too deep. At least some embodiments also include flexible wings that help stabilize the device on the neck during the procedure.

A first embodiment is a cricothyrotomy apparatus that includes a frame, a protuberance, and a blade member. The frame includes a blade guide. The protuberance extends in a first direction from the frame, and is located at a distance from the blade guide that corresponds to the distance between a sternal notch of an adult human and a cricothyroid membrane of the adult human. The protuberance is sized and configured to be at least partly received by a sternal notch of an adult human. The blade member is slideably disposed in the blade guide.

In another embodiment, the blade member and the blade guide are configured to arrest the travel of the blade member at a predetermined distance corresponding to an incision into the cricothyroid membrane when the frame is positioned or disposed on a human neck.

In a second embodiment, a cricothyrotomy apparatus include a blade member and a frame. The frame has a sternal notch alignment piece, and includes a channel for aligning the blade member. The frame further includes a connecting member between the sternal notch alignment piece and the channel. The blade member slidably moves within the channel.

The above-described features and advantages, as well as others, will become more readily apparent to those of ordinary skill in the art by reference to the following detailed description and accompanying drawings.

DETAILED DESCRIPTION

Figure 2:
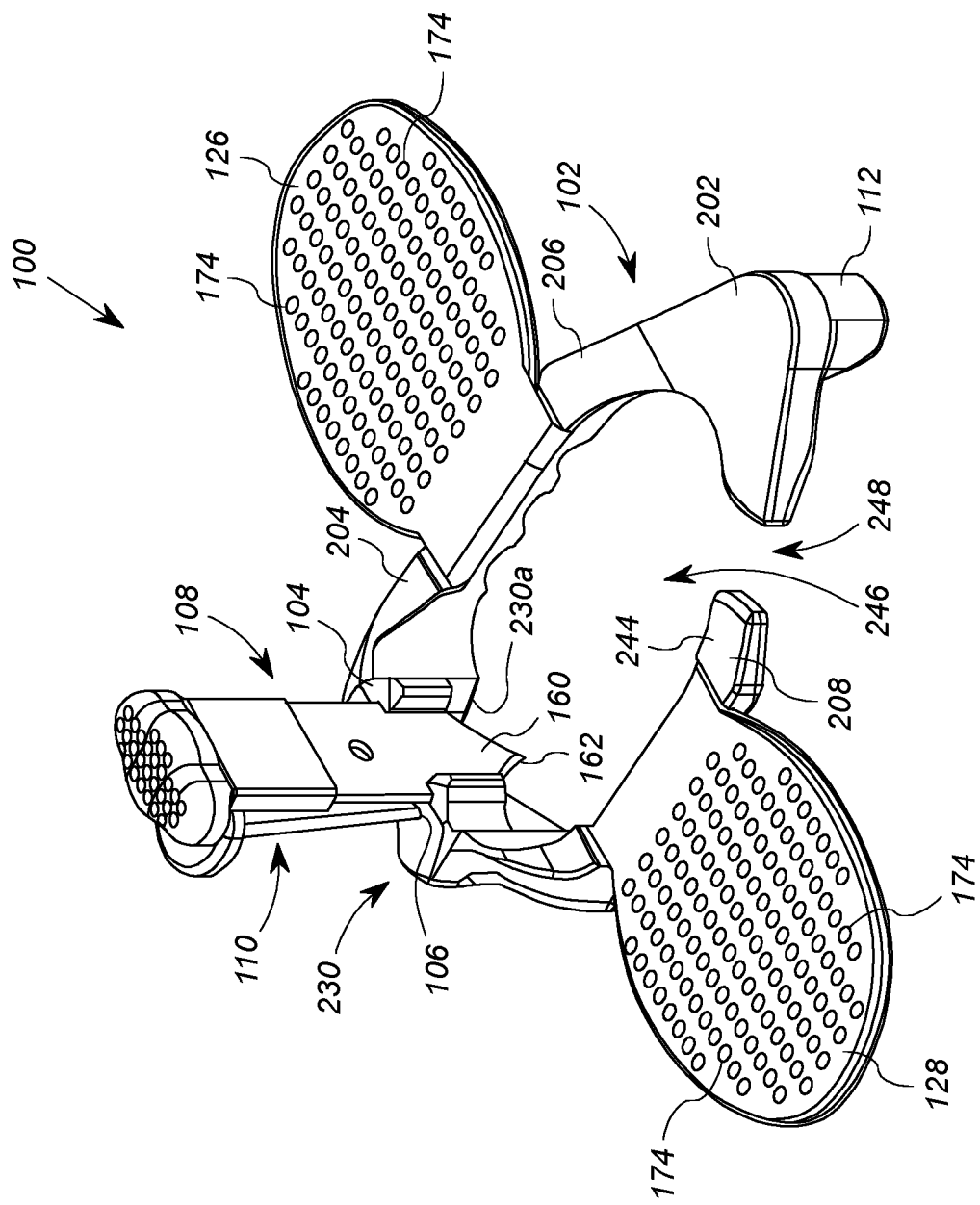
FIG. 2 shows a perspective view of a cricothyrotomy apparatus according to a first embodiment of the invention.
Figure 3:
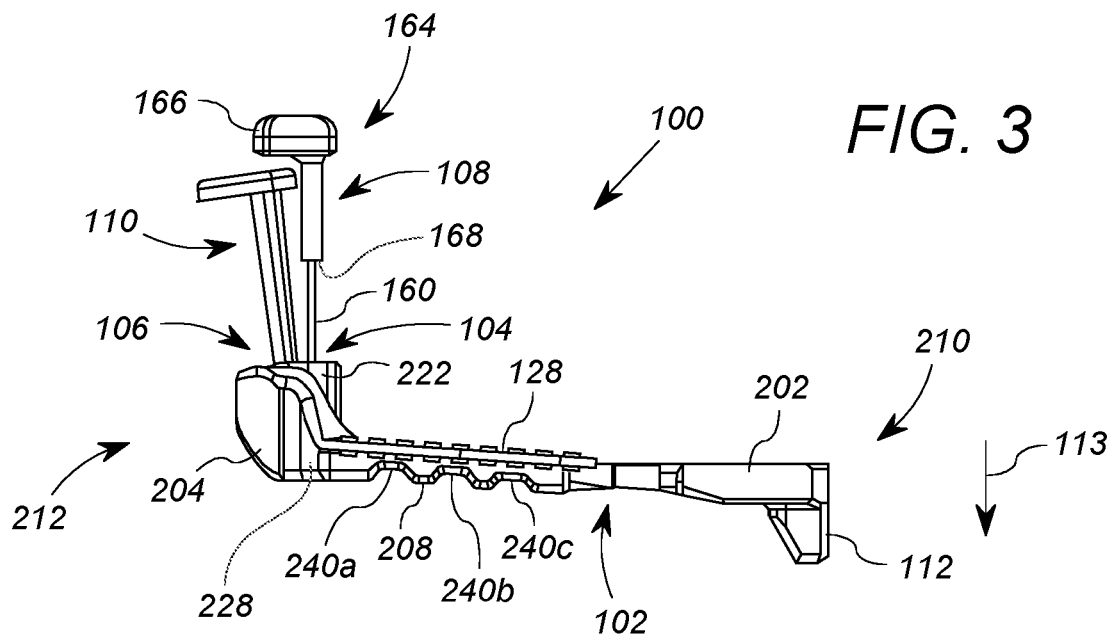
FIG. 3 shows a side plan view of the cricothyrotomy apparatus of FIG. 2.
Figure 4:
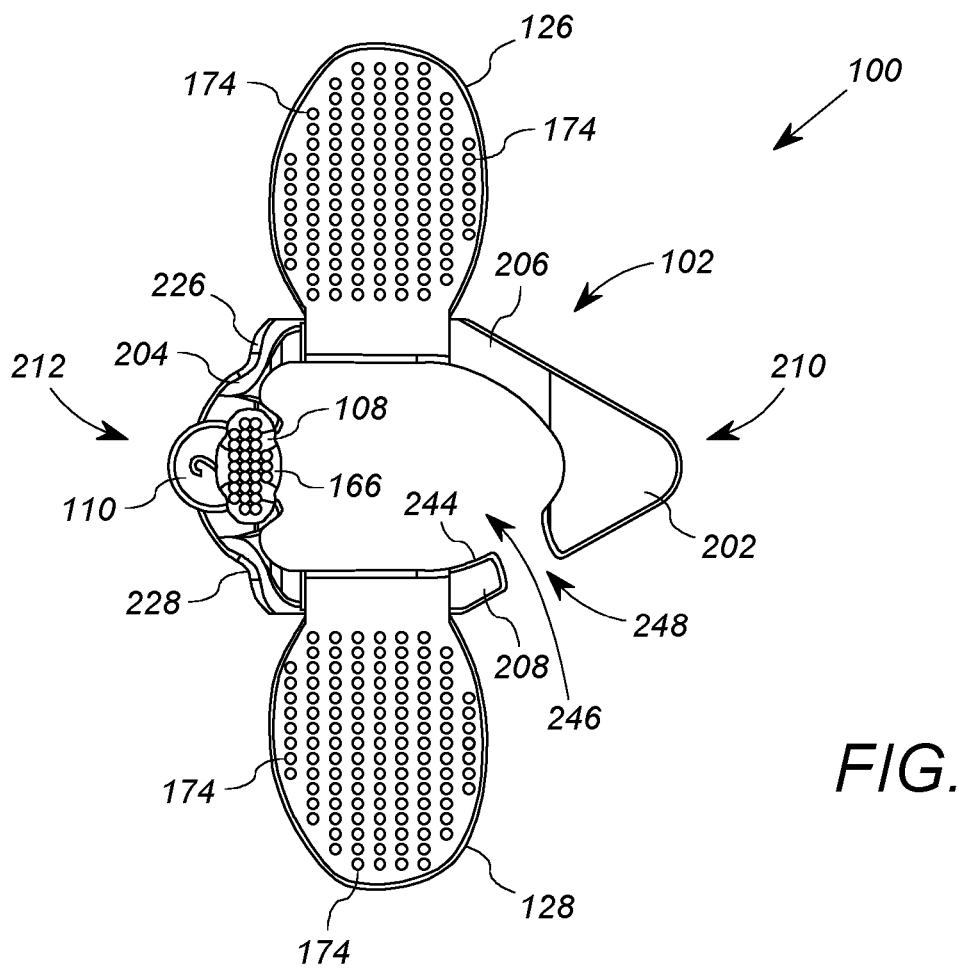
FIG. 4 shows a top plan view of the cricothyrotomy apparatus of FIG. 2.

FIG. 2 shows a perspective view of a cricothyrotomy apparatus 100 according to a first embodiment of the invention. FIG. 3 shows a side plan view of the apparatus, and FIG. 4 shows a top plan view of the apparatus. With contemporaneous reference to FIGS. 2-4, the apparatus 100 includes a frame 102, a blade member 108, a dilator 110, a sternal notch alignment piece 112, and first and second wings 126, 128. The frame 102 further includes a blade guide 104 and a dilator guide 106.

The sternal notch alignment piece 112 is a protuberance, for example, a knob or boss, extending in a first direction 113 from the frame. The protuberance 112 is located at a distance from the blade guide 104 that corresponds to the distance between a sternal notch of an adult human and a cricothyroid membrane of the adult human. The protuberance 112 is sized and configured to be at least partly received and seated by a sternal notch of an adult human, over the skin.

Figure 1:
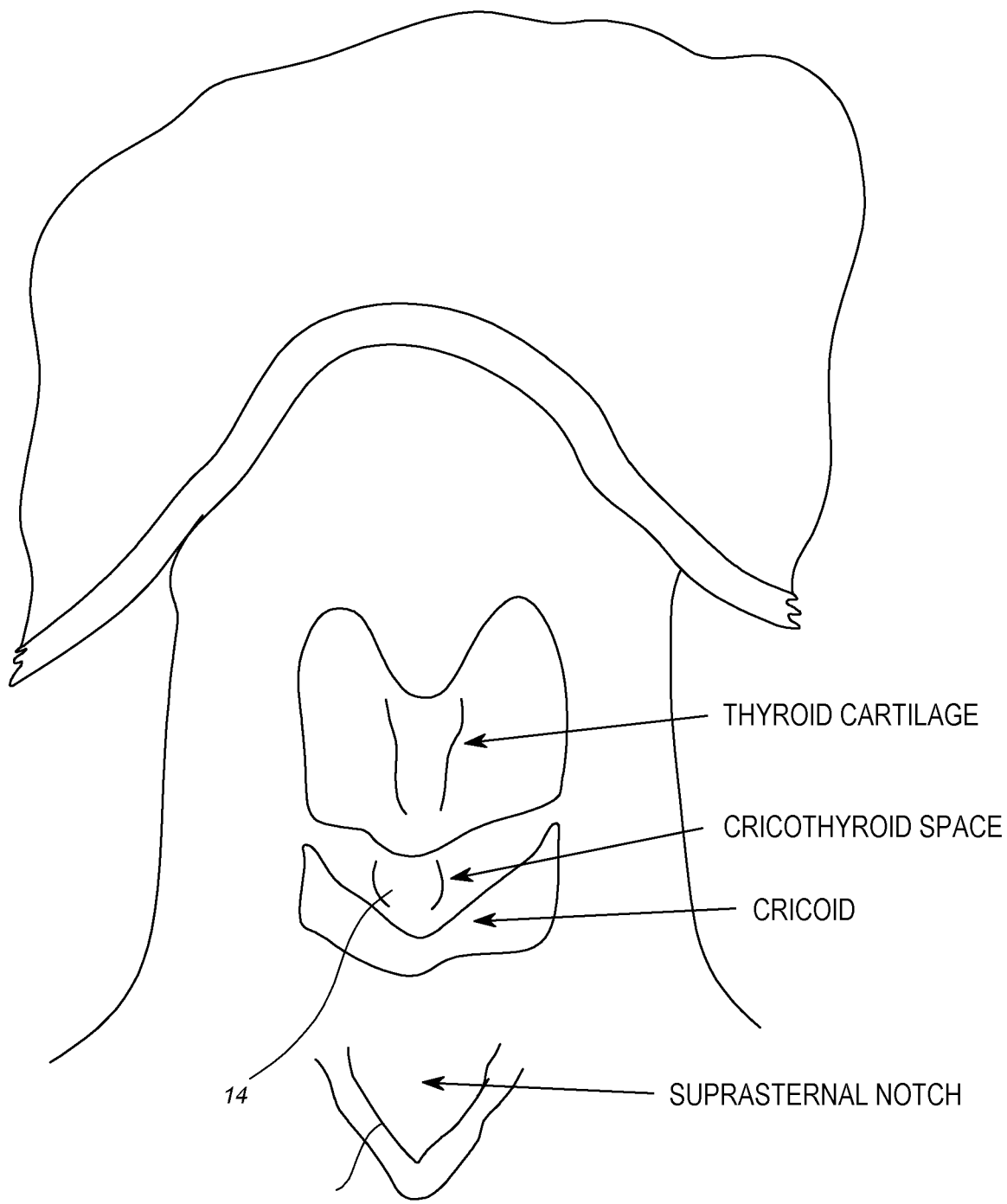
FIG. 1 shows a diagram of a neck of a human patient illustrating the location of the cricothyroid membrane.

Referring to FIG. 1, the suprasternal notch 12 of a human is located at the superior end of the sternum, and can be easily identified by touch at the base on the anterior portion of the neck. The cricothyroid membrane 14 is located, in adult humans, at a substantially uniform distance from the suprasternal notch 12, approximately 70 mm. Referring to FIGS. 1 to 4, the protuberance 112 and the blade guide 104 are configured such that when the protuberance 112 is seated within at least a portion of the sternal notch 12, the blade guide 104 is aligned over the cricothyroid membrane 14.

As used herein all references to relative positions and directions, namely, anterior, posterior, superior, inferior, medial and lateral, shall be with respect to the proper placement of the apparatus 100 on a human neck, such that the protuberance 112 is seated at least partially within the sternal notch 12, the blade guide 104 is disposed over the cricothyroid membrane 14, and the frame 102 extends long the neck portions in between the sternal notch 12 and the cricothyroid membrane 14.

Figure 8:
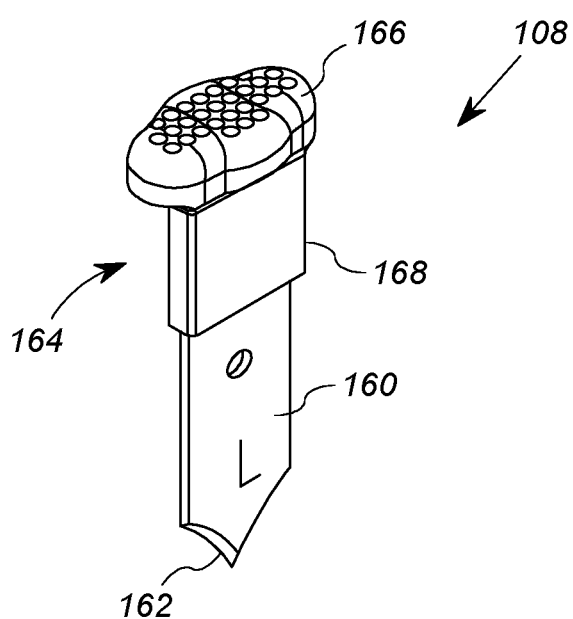
FIG. 8 shows a perspective view of an exemplary embodiment of the blade member of the cricothyrotomy apparatus of FIG. 2.

In this embodiment, the blade member 108 is slideably disposed within the blade guide 104. FIG. 8 shows a plan view of an exemplary blade member 108. The blade member 108 includes a blade 160 having an edge 162, and a handle portion 164 having a handle 166 and a shoulder 168. The blade member 108 may also includes a bulbous, non-sharp structure, not shown, on the side of the blade 160. The edge 162 preferably is substantially V-shaped along the width, thereby coming to a point, and is beveled along the thickness. The blade 160 may have a curved cross section in one embodiment, and a flat cross section in another embodiment.

Referring again to FIGS. 2-4, in addition to FIG. 8, the blade guide 104 retains the blade 160 in position, but allows for sliding movement of the blade 160 within the guide 104 in substantially the anterior-posterior direction. The shoulder 168 is configured to cooperate with the blade guide 104 to arrest a downward travel of the blade member 108 at a predetermined depth. The predetermined depth of travel distance of the blade member 108 corresponds to an incision by the blade 160 into the cricothyroid membrane when the frame 102 is disposed placed on a human with the protuberance 112 seated at least partly within the sternal notch 12 (see FIG. 1). The shoulder 168 is configured to interfere with the blade guide 104 such that the blade 160 punctures the cricothyroid membrane 14 but not the posterior thyroid cartilage. Further detail regarding the blade guide 104 is discussed further below in connection with FIGS. 5 and 6.

Figure 7:
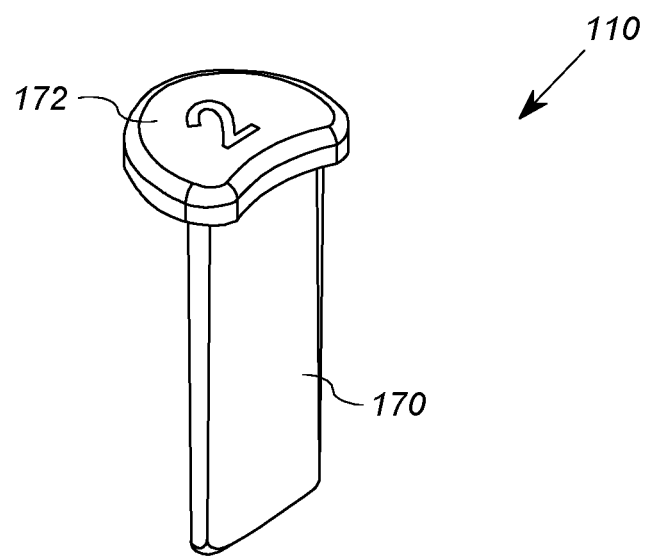
FIG. 7 shows a perspective view of an exemplary embodiment of the dilator of the cricothyrotomy apparatus of FIG. 2.

Referring to FIGS. 2, 3 and 7, the dilator 110 is a non-sharp, curved element that is preloaded into the dilator guide 106 of the frame 102 as shown in FIGS. 2 and 3. In general, the dilator 110 includes an elongate curved element 170 having a length comparable to that of the blade member 108, and a handle element 172 at one end. The dilator 110 may suitably be integrally formed of a rigid polymer. The dilator 110 is configured to be depressed (via the handle element 172) into the incision in the neck made by the blade member 108, either nearly at the same time as the incision, or after the blade edge 162 has passed into the neck. The dilator 110 is held inside the access hole in the tissue to maintain the hole before the breathing tube, not shown, is passed into the airway. The elongate curved member 170 of the dilator 110 acts as a backstop to direct the breathing tube into the airway.

Figure 5:
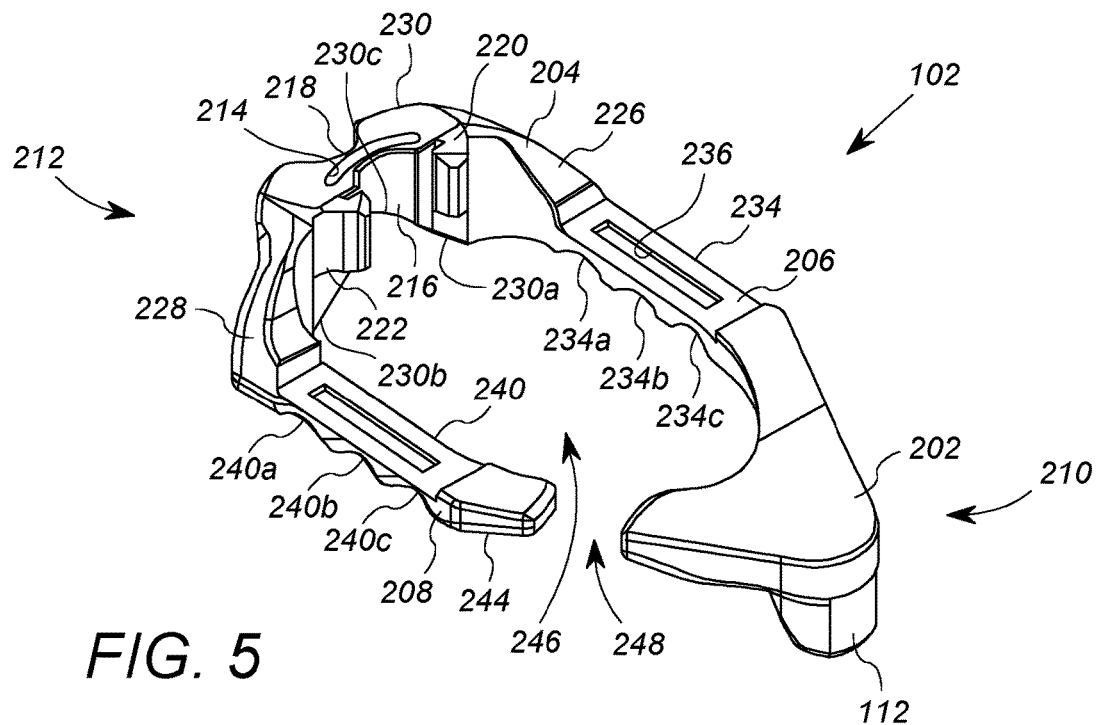
FIG. 5 shows a perspective view of exemplary frame of the cricothyrotomy apparatus of FIG. 2.
Figure 6:
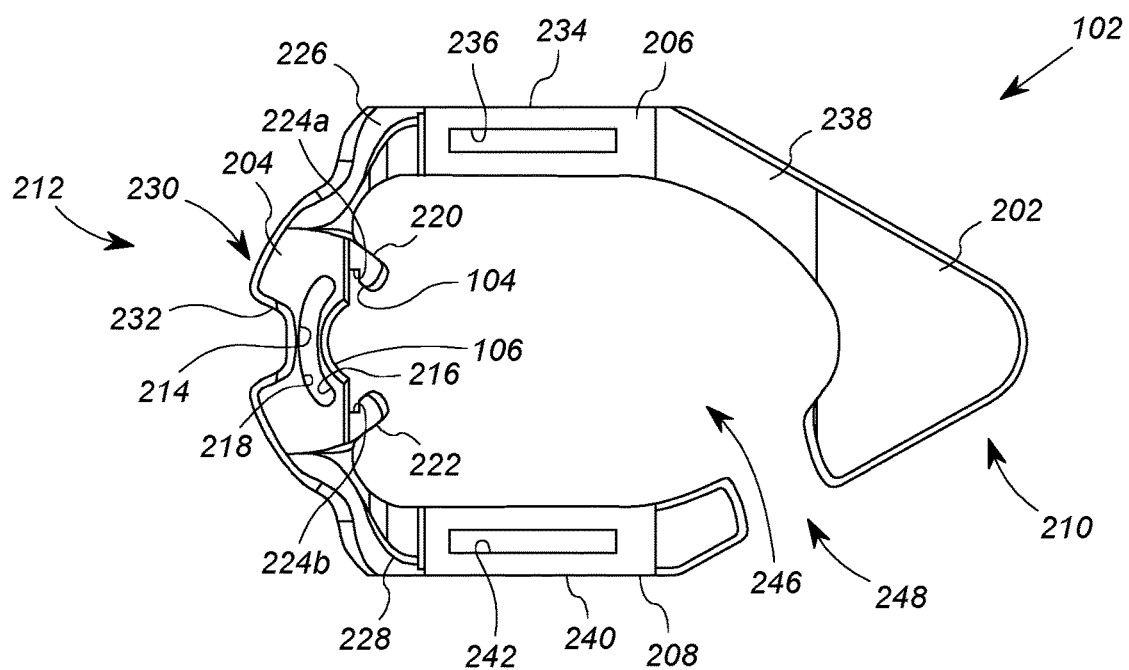
FIG. 6 shows a top plan view of the exemplary frame of FIG. 5.

FIG. 5 shows a perspective view of the frame 102 apart from the blade member 108, the dilator 110, and wings 126, 128 to provide additional clarity. FIG. 6 shows a plan view of the frame 102. With simultaneous reference to FIGS. 2, 5, and 6, the frame 102 includes a tail member 202, a jig 204, a first arm 206, a second arm 208. The tail member 202 is disposed at a first (inferior) end 210 of the frame 102, and the jig 204 is disposed at an opposing second (superior) end 212 of the frame 102. The protuberance 112 extends posteriorly from the tail member 202. The blade guide 104 and the dilator guide 106 are formed in the jig 204.

In particular, the jig 204 includes structural supports 226, 228 that extend medially, respectively, from the first arm 206 and second arm 208 to a central portion 230. The central portion 230 of the jig 204 includes the blade guide 104 and the dilator guide 106.

The dilator guide 106 is a sheath-like structure formed in the central portion of jig 204 having a curved channel 214 located medially on the jig 204. The channel 214 slightly concave toward the inferior direction, and forms a retaining channel for the elongate curved element 170 of the dilator 110, which is configured to slide in the anterior-posterior direction within the channel 214. (See FIG. 2). The channel 214 is largely formed by two spaced walls, an inferior wall 216 and a superior wall 218.

The central portion 230 of the jig 204 also includes two opposing notched extensions 220, 222 extending from the inferior wall 216. Each of the notched extensions 220, 222 define a corresponding notch 224a, 224b having open ends that face each other. The notches 224a and 224b collectively form the blade channel of the blade guide 104. The notched extensions 220, 222 cooperate with the blade shoulder 168 to limit the posterior travel of the blade 160. (See also FIGS. 3 and 8). The blade 160 otherwise slideably moves within the blade channel notches 224a, 224b when manipulated by the handle 166. The blade 160 is configured to seat within the channel notches 224a, 224b without sliding in the absence of applied pressure, using tension and/or stiction. To this end, the blade 160 may have a width that slightly exceeds that of the channel defined by the notches 224a, 224b.

The rear wall, or superior wall of the central portion 230 includes a medial notch 232 that allows for digital manipulation of the handle element 172 of the dilator 110 and blade handle 166. The bottom wall of the central portion 230 includes opposing inclined portions 230a, 230b and rounded concave intersection 230c therebetween. The portions 230a, 230b, and 230c collectively define a posterior facing curve in the bottom that can be used to help seat the frame 102 medial-laterally on the thyroid/neck. Thus, this curve 230a, 230b, and 230c, in combination with the protuberance 112, assist in proper placement of the apparatus 100 on the human neck.

The first arm 206 extends from the first end 210 of the frame 102 to the second end 212 of the frame 102. More specifically, the first arm 206 extends from the support element 226 of the jig 204 to the tail member 202. In this embodiment, the first arm 206 forms the structural member that connects, and thus defines the spacing between, the protuberance 112 on the tail member 202 and the blade guide 104 of the jig 204. The first arm 206 includes a straight beam 234 extending substantially in the inferior direction from the end of the support member 226. The straight beam 234 includes a central throughhole 236 which allows for the secure, overmolded, connection of the first wing 126. The underside of the straight beam 234 has a series of three concave depressions 234a, 234b, 234c. The first arm 206 also include a connector beam 238 that extends at an angle from the end of the straight beam 234 to the tail member 202.

In this embodiment, the second arm 208 forms the structural member that provides support, but does not connect the tail member 202 and the the jig 204. The second arm 208 includes a straight beam 240 extending substantially in the inferior direction from the end of the support member 228.

The straight beam 240 is substantially identical to the straight beam 234, and thus also includes a central throughhole 242 which allows for the secure, overmolded, connection to the second wing 128. The underside of the straight beam 240 has its own series of three concave depressions 240a, 240b, 240c. The second arm 208 also includes a nub 244 of a connector beam that extends at an angle from the end of the straight beam 240, but stops short of the tail member 202.

The first arm 206 and second arm 208 thereby form a partial lateral enclosure around an open interior 246 of the frame 102. The discontinuity or void 248 formed between the nub 244 and the tail member 202 defines a passage through which a breathing tube, not shown, may pass out of the open interior 246 when the breathing tube is in place in the patient. This allows the apparatus 100 to be easily removed by lateral movement after the tube is inserted into the opening in the neck formed by the blade member 108 and dilator 110. Thus, the void 248 has a width that exceeds that of a breathing tube used for cricothyromies, the width of which would be known to those of ordinary skill in the art.

Referring again primarily to FIGS. 2 to 4, the wings 126, 128 are semi-rigid, non-stretching, slightly tacky wings or flaps configured to inhibit slippage of the apparatus 100 device during the procedure. The flexible wings 126, 128 are preferably formed by overmolding onto the more rigid frame 102. In this embodiment, the first wing 126 includes a two to four inch flap having rows and columns of indentations 174 to aid in gripping strength. The second wing 128 has a substantially analogous structure.

In operation, the apparatus 100 is packaged for use such that the blade member 108 is preloaded in a blade guide 104 and the dilator 110 is preloaded in the dilator channel 106 as shown in FIGS. 2-4. To perform the procedure, the user first positions the preloaded apparatus 100 on the patient. To this end, the user aligns the frame 102 on the patient (see FIG. 1) using the protuberance 112, which seats in the sternal notch 14 of a patient. The user also seats the curve on the bottom wall of the central portion 230 on the trachea. The user then presses down on the wings 126, 128 to hold the frame 102 stable in position during the incision and tube insertion procedure. In position, the frame 102 seats along the midline of the neck across the trachea of a patient, such that all or part of the concave depressions 234a, 234b, 234c of the first arm 234 and the corresponding depressions 240a, 240b and 240c on the second arm 240 contact the skin. It will be appreciated that the open interior 246 allows for the neck to be visible and palpated while the apparatus 100 is held to the anatomy.

With the apparatus 100 in position (with the protuberance 112 seated at least in part in the sternal notch 12), the user depresses the blade member 108 (via handle 166) such that it travels posteriorly along the channel 224a, 224b of the blade guide 104, keeping the apparatus 100 aligned as the blade 160 is pressed into the tissue. The travel of the blade member 108 stops at a predetermined depth when the shoulder 168 strikes the notched extensions 220, 222. It will be appreciated that interfering features of the blade member 108 and the blade guide 104 that stop the travel of the blade member 108 may take other suitable forms. In any event, the blade 160, shoulder 168 and blade guide 104 are configured such that the blade edge 162 does not perforate the posterior trachea. The blade 160 is designed to operate is a certain depth to allow cutting through overlying tissue anterior to the cricothyroid membrane and into the hollow cavity in the trachea.

The user depresses the dilator 110 (via handle 172) into the neck opening created by the blade 160 either at nearly the same time as the blade member 108, or after the blade edge 162 has passed into the neck. The dilator 110 is held inside the access hole in the tissue to maintain the hole before the breathing tube is passed into the airway.

The user then lifts the blade handle 166 to remove the blade 160 following the perforating procedure. The dilator 110 remains in place with the blade 160 removed to keep the airway open for placement of the breathing tube, or tracheal tube. Once the blade 160 is removed, the tracheal tube is placed into the patient's airway with the dilator 110 to guide the tube into the appropriate position in the patient's trachea. The user may then use the handle 172 to remove the dilator 110 from the patient's anatomy once the tube has been inserted into the trachea. Thereafter, the frame 102 may be moved away from the patient by laterally moving the frame 102 such that the in-place tube passes through the void 248.

The tube or breathing tube referred to herein may suitably be a 220 mm long polymer tube suitable for use for oral and nasal intubation and which has an inner diameter of 5.5 mm to 7.0 mm, and preferably 6.0 mm or 6.5 mm. The tube may also include an inflatable outer bag (and corresponding inflator) near the distal end which may be inflated to block the airway above the insertion site to ensure a direct pathway between the lungs and the operative end of the tube. Such tubes for use in cricothyrotomies are known to those of ordinary skill in the art. The tube in one embodiment also includes a throughhole in the side, between the distal end and the inflatable outer bag.

Figure 9:
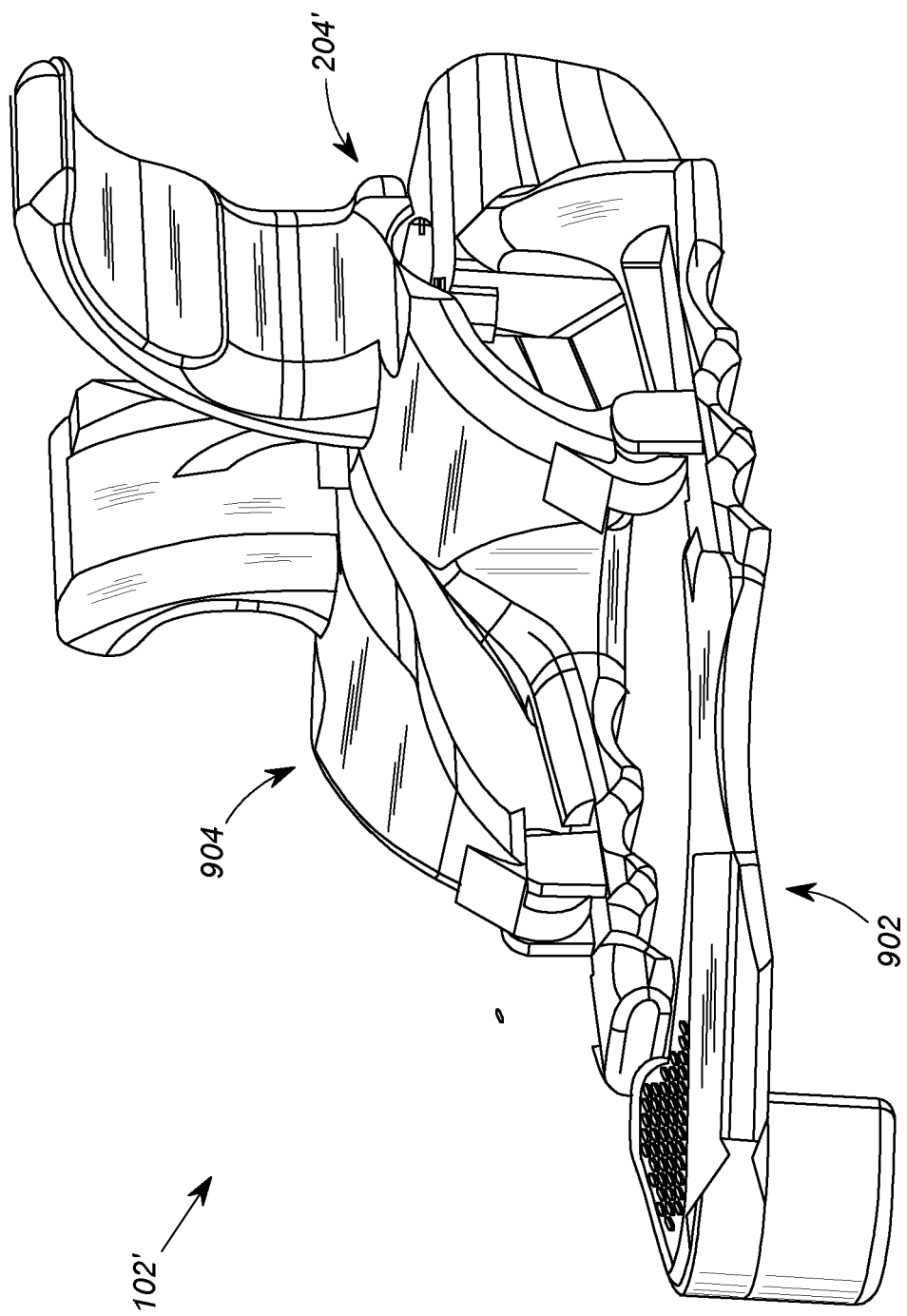
FIG. 9 shows an alternative embodiment of a frame that may be used in cricothyrotomy apparatus according to the invention.

Another embodiment employs a hinged version of the jig 204. A perspective view of the frame 102' of this embodiment is shown in FIG. 9. In this embodiment, a first plastic element 902 including the arms 206', 208' and the tail member 202' of the frame 102' are rotatably attached (detachably or permanently) to a second plastic element 904 that includes the jig 204' that holds the blade and dilator, not shown in FIG. 9. In this embodiment, the jig 204' has the same structural features of the blade guide 104 and dilator guide 106, not shown in FIG. 9. The jig 204' may also have features capable of holding a preloaded breathing tube. The jig 204' may otherwise have the same structures and operation as the jig 204 of FIGS. 2-6, discussed above.

The cricothyrotomy apparatus and procedure discussed above may be used during emergency when other forms of establishing an airway are not possible or contraindicated. Such conditions may arise at a battlefield, in an ambulance, or at the site of the injury. One advantage of some embodiments is that the system provides a compact, low-cost, intuitive device that allows the user to make an accurate incision and quickly insert the tube into the patient's airway. The device uses a common physiological landmark, the sternal notch, to consistently locate the device across all body types. The device is lightweight, low profile, and intuitive.

The frame 102 is preferably formed by injection molding of a hard polymer such as a polycarbonate ABS alloy. The wings 126, 128 are overmolded onto the frame 102 and are formed of a soft, tacky polymer such as a thermoplastic urethane. The blade member 108 and the dilator 110 are separately formed using conventional techniques. The blade member 108 and the dilator 110 are at least partially inserted into the frame 102 before use, such that the apparatus 100 has a single piece construction that is ready to use.

It will be appreciated that the above-described embodiments are merely illustrative, and that those of ordinary skill in the art may readily define their own implementations and modifications that incorporate the principles of the present invention and fall within the spirit and scope thereof.

What is claimed is:

1. A cricothyrotomy apparatus, comprising:
a frame including a blade guide;
a protuberance extending in a first direction from the frame, the protuberance located at a distance from the blade guide that corresponds to the distance between a sternal notch of an adult human and an anterior cricothyroid membrane of the adult human, the protuberance being sized and configured to be at least partly received by a sternal notch of an adult human; and
a blade member slideably disposed in the blade guide.

2. The cricothyrotomy apparatus of claim 1, wherein:
the frame includes a first end, a second end, and at least a first arm extending therebetween;
the protuberance extends from the frame at the first end, and the blade guide is disposed proximate the second end.

3. The cricothyrotomy apparatus of claim 2, further comprising a second arm extending at least partially between the first end and the second end, defining an open interior between the first arm and the second arm.

4. The cricothyrotomy apparatus of claim 3, wherein the first end, the second end, the first arm and the second arm form a partial surround around the open interior, the partial surround having a void, the void having a width exceeding a width of breathing tube.

5. The cricothyrotomy apparatus of claim 3, wherein the blade guide is rotatably attached to at least one of the first arm, the second arm, the first end, and the second end.

6. The cricothyrotomy apparatus of claim 1, wherein the blade member includes a blade edge and a shoulder, the shoulder configured to cooperate with the blade guide to arrest a downward travel of the blade member at a predetermined depth.

7. The cricothyrotomy apparatus of claim 6, wherein the blade edge is V-shaped along a width thereof.

8. The cricothyrotomy apparatus of claim 1, wherein the frame further comprises a dilator guide disposed proximate the blade guide, and further comprising a dilator slidably disposed within the dilator guide.

9. A cricothyrotomy apparatus, comprising:
a frame including a blade guide; and
a protuberance extending in a first direction from the frame, the protuberance located at a distance from the blade guide corresponding to the distance between a sternal notch of an adult human and an anterior cricothyroid membrane of the adult human, the protuberance being sized and configured to be at least partly received by a sternal notch of an adult human;
a blade member slideably disposed in the blade guide, the blade member and the blade guide configured to arrest the travel of the blade member at a predetermined distance corresponding to an incision into the cricothyroid membrane when the frame is disposed on a human.

10. The cricothyrotomy apparatus of claim 9, further comprising flexible flaps extending laterally outward from opposing sides of the frame.

11. The cricothyrotomy apparatus of claim 10, wherein:
the frame includes a first end, a second end, and at least a first arm extending therebetween;
the protuberance extends from the frame at the first end, and the blade guide is disposed proximate the second end.

12. The cricothyrotomy apparatus of claim 11, further comprising a second arm extending at least partially between the first end and the second end, defining an open interior between the first arm and the second arm, and wherein each of the flexible flaps extends laterally from a corresponding one of the first arm and the second arm.

13. The cricothyrotomy apparatus of claim 12, wherein the first end, the second end, the first arm and the second arm form a partial surround around the open interior, the partial surround having a void, the void having a width exceed a width of breathing tube.

14. A cricothyrotomy apparatus, comprising:
   a blade member; and
   a frame with a sternal notch alignment piece, the frame including a channel for aligning the blade member, the frame further including a connecting member between the sternal notch alignment piece and the channel; and
   a plurality of flaps coupled to and extending outward from the frame;
   wherein
   the blade member slidably moves along and against the frame within the channel.

15. The apparatus of claim 14, wherein the frame further comprises a thyroid alignment curve.

16. The apparatus of claim 14, further comprising a dilator and a dilator channel slideably receiving and aligning the dilator.

17. The apparatus of claim 14, wherein at least a portion of the blade member has a pointed V-shaped edge surface.

18. The apparatus of claim 17, wherein the blade member includes a handle portion and a shoulder, the shoulder configured to engage a portion of the frame to arrest a travel of the blade member within the channel.

19. The apparatus of claim 18, further comprising a dilator and a dilator channel slideably receiving and aligning the dilator.

20. The apparatus of claim 14, wherein the blade member includes a handle portion and a shoulder, the shoulder configured to engage a portion of the frame to arrest a travel of the blade member within the channel.

* * * * *